(12) United States Patent
Gilbert

(10) Patent No.: US 6,381,576 B1
(45) Date of Patent: Apr. 30, 2002

(54) METHOD, APPARATUS, AND DATA STRUCTURE FOR CAPTURING AND REPRESENTING DIAGNOSTIC, TREATMENT, COSTS, AND OUTCOMES INFORMATION IN A FORM SUITABLE FOR EFFECTIVE ANALYSIS AND HEALTH CARE GUIDANCE

(76) Inventor: Edward Howard Gilbert, 5716 Seville Ct., Plano, TX (US) 75093

( * ) Notice: Subject to any disclaimer, the term of this patent is extended or adjusted under 35 U.S.C. 154(b) by 0 days.

(21) Appl. No.: 09/212,521

(22) Filed: Dec. 16, 1998

(51) Int. Cl.7 .............................................. G06F 17/60
(52) U.S. Cl. .......................................... 705/2; 600/300
(58) Field of Search ...................... 705/2, 3, 4; 600/300

(56) References Cited

U.S. PATENT DOCUMENTS

| | | | |
|---|---|---|---|
| 4,731,725 A | 3/1988 | Suto et al. ................... | 364/415 |
| 4,733,354 A | 3/1988 | Potter et al. ................. | 364/415 |

(List continued on next page.)

FOREIGN PATENT DOCUMENTS

| FR | WO 92/13322 | * | 1/1992 | ......................... 7/8 |
|---|---|---|---|---|
| JP | 360101667 A | * | 11/1983 | ................. 600/300 |

OTHER PUBLICATIONS

Business Insurance "Bi Directory of Risk Management Information Systems" p. 30, Dec. 7, 1998.*

*Primary Examiner*—Frantzy Poinvil
*Assistant Examiner*—S Wasylchak
(74) *Attorney, Agent, or Firm*—Max Ciccarelli; Matthew S. Anderson; Thompson & Knight LLP

(57) ABSTRACT

A diagnostic and treatment information data structure encapsulates, with or without identifying a specific patient, information regarding a particular diagnosis-treatment cycle for an individual patient. The diagnostic and treatment information data structures for a number of diagnosis-treatment cycle may be combined within a database for analysis in outcomes or cost effectiveness studies. A relational database which assists the health care provider in formulating the diagnostic and treatment information data structure for a specific diagnosis-treatment cycle can, within a user interface, display information determined during the outcomes or cost effectiveness studies to influence the health care provider at the point of decision. Effective analyses of diagnostic, treatment, and outcomes information and guidance for health care professionals based on such analyses is thus facilitated. An Internet/intranet database program employing the diagnostic and treatment information data structure contains both clinical and financial information permitting effective filtering and analysis of CPT codes as to accuracy and appropriateness.

20 Claims, 7 Drawing Sheets

U.S. PATENT DOCUMENTS

| | | | | |
|---|---|---|---|---|
| 4,839,822 A | | 6/1989 | Dormond et al. | 364/513 |
| 5,262,943 A | | 11/1993 | Thibado et al. | 364/413.01 |
| 5,301,105 A | * | 4/1994 | Cummings | 364/401 |
| 5,307,262 A | * | 4/1994 | Ertez | 364/413.01 |
| 5,325,293 A | * | 6/1994 | Dorne | 364/413.01 |
| 5,327,341 A | * | 7/1994 | Whalen et al. | 364/413 |
| 5,471,382 A | | 11/1995 | Tallman et al. | 364/406 |
| 5,483,443 A | | 1/1996 | Milstein et al. | 364/401 |
| 5,517,405 A | * | 5/1996 | McAndrew et al. | 364/401 |
| 5,519,607 A | | 5/1996 | Tawil | 364/401 |
| 5,557,514 A | * | 9/1996 | Seare et al. | 364/401 |
| 5,583,758 A | * | 12/1996 | McIlroy et al. | 395/202 |
| 5,764,923 A | | 6/1998 | Tallman et al. | 395/203 |
| 5,778,345 A | | 7/1998 | McCartney | 705/2 |
| 5,786,816 A | | 7/1998 | Macrae et al. | 345/339 |
| 5,794,208 A | * | 8/1998 | Goltra | 705/2 |
| 5,809,476 A | | 9/1998 | Ryan | 705/2 |
| 5,812,984 A | * | 9/1998 | Goltra | 705/3 |
| 5,826,237 A | | 10/1998 | Macrae et al. | 705/2 |
| 5,845,254 A | * | 12/1998 | Lockwood et al. | 705/2 |
| 5,899,998 A | * | 5/1999 | McGauley et al. | 707/104 |
| 5,918,208 A | * | 6/1999 | Javitt | 705/2 |
| 5,930,759 A | * | 7/1999 | Moore et al. | 705/2 |
| 5,924,074 A | * | 8/1999 | Evans | 705/3 |
| 5,933,809 A | * | 8/1999 | Hunt et al. | 705/3 |
| 5,940,802 A | * | 8/1999 | Hildebrand et al. | 705/3 |
| 5,953,704 A | * | 9/1999 | McIlroy et al. | 705/2 |
| 5,956,690 A | * | 9/1999 | Haggerson et al. | 705/3 |
| 5,970,463 A | * | 10/1999 | Cave et al. | 705/3 |
| 5,974,389 A | * | 10/1999 | Clark et al. | 705/3 |
| 5,991,729 A | * | 11/1999 | Barry et al. | 705/3 |
| 5,991,730 A | * | 11/1999 | Lubin et al. | 705/3 |
| 6,047,259 A | * | 4/2000 | Campbell et al. | 705/3 |
| 6,151,581 A | * | 11/2000 | Kraftson et al. | 705/3 |
| 6,154,726 A | * | 11/2000 | Rensimer et al. | 705/2 |

* cited by examiner

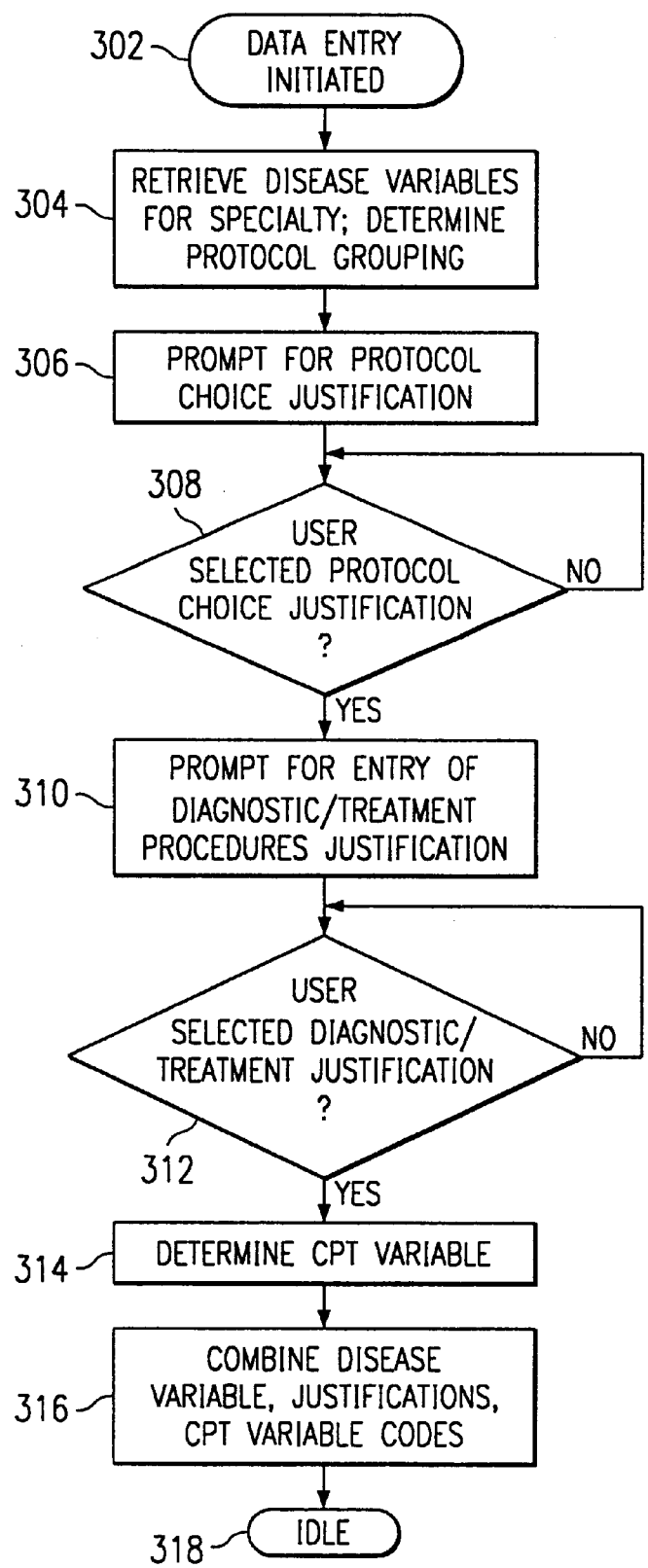

METHOD, APPARATUS, AND DATA STRUCTURE FOR CAPTURING AND REPRESENTING DIAGNOSTIC, TREATMENT, COSTS, AND OUTCOMES INFORMATION IN A FORM SUITABLE FOR EFFECTIVE ANALYSIS AND HEALTH CARE GUIDANCE

BACKGROUND OF THE INVENTION

1. Technical Field

The present invention relates generally to capturing diagnostic and treatment information for individual diagnosis-treatment cycles and in particular to capturing such diagnostic and treatment information in a form suitable for effective analysis across multiple diagnosis-treatment cycle instances and providing guidance to a health care provider at the point of decision in a subsequent diagnosis-treatment cycle. Still more particularly, the present invention relates to a novel data structure capturing cost information, protocol treatment choices and rationales together with initial disease variable values and outcomes to permit both effective analysis and development of treatment guidelines. Codes may be effectively transferred onto the superbill and may be employed to facilitate or bypass the authorization process for insurance companies. Codes may provide an effective means of transferring data between dissimilar health and billing information systems, and for documenting the health care process to facilitate regulatory guideline compliance.

2. Description of the Related Art

Allocation of health care resources to individuals in a cost effective manner without compromise to outcomes and quality has become a significant issue in contemporary society. A movement exists to establish standards of care to assure that the highest quality of medicine is practiced in a uniform manner. These standards of care may include written protocols and practice guidelines or priority and appropriateness rankings promulgated by organizations, and/or priorities of diagnostics and treatment to be followed by individual health care providers. To successfully establish standards of care, however, diagnostic and treatment information must be both successfully captured in a form suitable for effective analysis and provided to the health care provider at the point of decision.

The capture of diagnostic and treatment information is impeded by the extreme degree of complexity associated with outcome data and their measurement and reliability. While theoretical models attempt to simplify the measurement tools for outcome analysis, outcomes are not simply "cured" versus "not cured" propositions, but instead include variables driven by issues such as quality of life, increased longevity, complications, and side effects. To compensate, some methodologies factor such variables into the outcome measurement to derive "quality adjusted" results. This factoring makes it difficult to formulate specific recommendations for individual cases.

Currently, ICD9 codes, which are general descriptions of the disease process, and CPT and DRG billing codes are the only information typically available for analysis of individual diagnostic-treatment cycles. Attempts to retrospectively obtain data necessary for effective analysis, such as the rationale for a particular treatment choice, is extremely difficult since such information is not normally captured. Thus medical societies, which typically gather only measurement data, and the insurance industry, which is substantially constrained to analyzing information provided with billing records, are generally unable to obtain this information for analysis.

Early attempts at an Electronic Medical Record have taken the form of simply converting the paper chart to a paperless chart contained in a medical electronic medical record database. Since much of the record is in text form, analysis of clinical data is hampered by inconsistent data entry, the absence of relationships between the data collected, and the lack of consistent vocabularies allowing comparison between and among systems. Consistent data fields are largely demographic in nature rather than oriented to clinical research. While the need for consistent database fields to support data analysis has been recently recognized, and some medical societies are developing outcome study databases for the relevant specialty, no effort has been undertaken to capture specific and accurate clinical and cost information for diagnostics and treatments based on specific disease issues. Such information is necessary for effective analysis both within specialties and globally across all specialties. Clinical and costs analyses of outcome data would benefit both the health care profession and insurance providers.

For effective use, clinical and cost information from prior diagnostic-treatment cycles must also be provided to health care professionals at the point of decision. Customary practices are difficult to influence or alter without the ability to offer suggestions at the time the customary practice is performed.

Additionally, there are no current mechanisms in place to check CPT billing codes for inaccuracy and abuse, other than random individual hand chart reviews, which may be both tedious and erratic and is impossible to perform with any significant volume of diagnostic-treatment information.

It would be desirable, therefore, to provide a data structure for capturing diagnostic-treatment information for effective analysis and for guidance of health care providers at the point of decision. Further, the paramount need for CPT code inaccuracy and abuse detection is satisfied. The availability in the present invention of disease and protocol variables for cross-matching with CPT code variables permits significant analysis and filtering of CPT codes.

SUMMARY OF THE INVENTION

A diagnostic and treatment information data structure includes: a disease variable code documenting the variables for a disease process which are important to a particular medical specialty; an optional protocol grouping code identifying priorities assigned by a specialty-specific medical society or other organization to available diag-nostic and treatment protocol choices base on measured disease variable values; a protocol choice code identifying the diagnostic and treatment regime selected by the health care provider, preferably integrated into a justification code identifying a rationale advanced by the health care provider for choosing the selected protocol choice; a diagnostic/treatment justification code for each procedure, diagnostic study, and treatment ordered for the disease process, containing the rationale of the health care provider in ordering the procedure, study or treatment and the priority assigned to the procedure, study or treatment by the medical societies; and a CPT variable code identifying billing for procedures which may be cross-correlated and checked against the disease variables, protocol choice, and diagnostic/treatment justifications. The diagnostic and treatment information data structure thus encapsulates, without identifying a specific patient, information regarding a particular diagnosis-treatment cycle for an individual patient. The diagnostic and treatment information data structures for a number of diagnosis-treatment cycle may be combined within a database for analysis in outcomes or cost effectiveness studies. A relational database which assists the health care provider in formulating the diagnostic and treatment information data structure for a specific diagnosis-treatment cycle may, within a user interface, display information determined during the outcomes or cost effectiveness studies to influence the health care provider at the point of decision, and may serve to satisfy the documentation requirements being mandated by regulatory organizations. Effective analyses of diagnostic, treatment, and outcomes information and guidance for health care professionals based on such analyses is thus facilitated. An Internet/intranet database program employing the diagnostic and treatment information data structure contains both clinical and financial information permitting effective filtering of CPT codes as to accuracy and appropriateness.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

FIG. 3 depicts a high level flowchart for a process of formulating a diagnostic and treatment information data structure in accordance with a preferred embodiment of the present invention;

DETAILED DESCRIPTION

Figure 1:
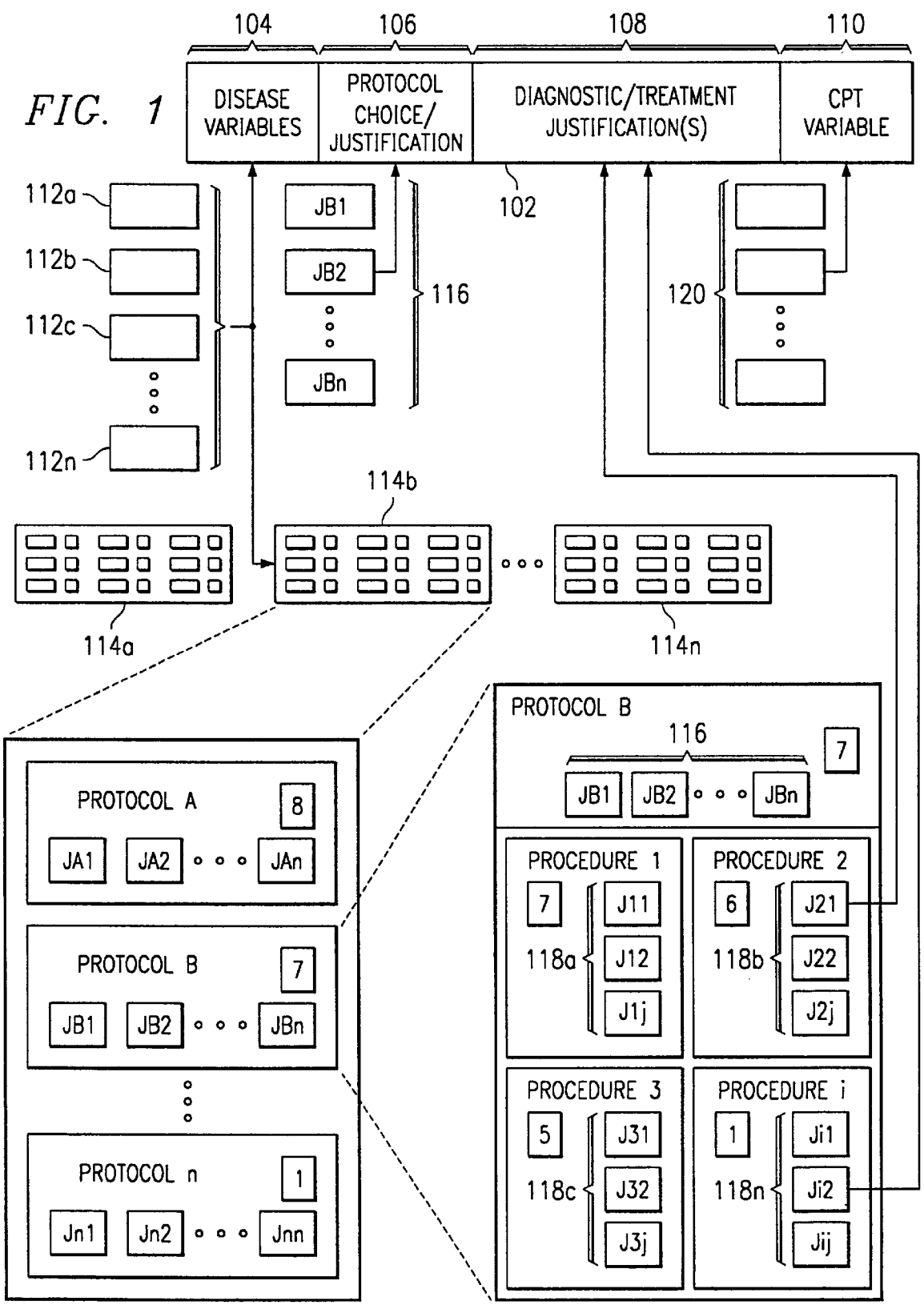
FIG. 1 depicts a data structure containing diagnostic and treatment information in accordance with a preferred embodiment of the present invention.

With reference now to the figures, and in particular with reference to FIG. 1, a data structure containing diagnostic and treatment information in accordance with a preferred embodiment of the present invention is depicted. Data structure 102 encapsulates demographic, location, physician, specialty, testing, diagnostic, and treatment information concerning a particular diagnosis-treatment cycle for an individual medical problem experienced by an individual patient. Data structure 102 includes a plurality of subcodes or fields including disease variable(s) (vcode) field 104, protocol choice justification field 106, diagnostic/treatment procedure(s) justification field 108, and CPT variable field 110.

Vcode field 104 contains a unique code for a set of critical disease variables 112a–112n adapted for the specialty of the health care provider performing the diagnosis-treatment cycle for the respective patient. Different specialties rely on different diagnostic information in selecting treatment. In breast cancer, for example, tumor margins are of important significance to the surgical and radiation oncologists, but less important to the medical oncologist; menopausal status, on the other hand, is of substantially greater importance to the medical oncology specialty than to the surgical and radiation oncology specialties. Accordingly, the critical disease variables 112a–112n employed to generate the contents of vcode field 104 are selected from the overall patient diagnostic testing information depending on the specialty of the health care provider. The group of approximately 3–7 critical disease variables 112a–112n employed is preselected based on the standard practices of the corresponding specialty.

The test results from corresponding tests on the patient are entered into disease variables 112a–112n, and 5 the ranges within which the test results fall are encoded as a unique code in vcode field 104. The data entered into disease variables 112a–112n is also employed to select a protocol grouping for various possible treatment protocols. For this purpose, possible test results for each disease variable 112a–112n should be grouped based on specified ranges or cutoff information supported by outcomes research. For instance, with respect to prostate cancer, the pathologic Gleason grading of 3 to 10 may be grouped into four ranges for that variable: Gleason 3–4, Gleason 5–6, Gleason 7, and Gleason 8–10. These aggregates are supported by outcomes research in prostate cancer. Therefore, an actual measured result (e.g., Gleason 6) would be compared to these ranges and employed to select a protocol grouping 114a–114n.

Other critical variables for prostate cancer for radiation therapy include the disease stage, the patient's age, and the PSA blood value. However, as the number of disease variables and/or ranges within a disease variable increases, the number of possible protocol groupings also increases. The number of unique permutations possible for all disease variables can thus quickly grow to between about 250 and 500 combinations. While this number of permutations is manageable for analysis and reporting, it is hardly useful for diagnosis and treatment. Therefore, each possible combination of disease variables is assigned to one of approximately 10–12 protocol groupings 114a–114n, roughly correlating to the generally accepted diagnostic practices of most members of the relevant specialty. In practice, the protocol groupings are preferably formulated and/or approved by the professional medical society associated with the relevant specialty, in a manner analogous to the limited efforts undertaken in the American College of Radiology's Appropriateness Criteria Project. Rather than addressing only a limited number of variants, however, a comprehensive treatment of all possible permutations is preferred within protocol groupings 114a–114n.

Each protocol grouping 114a–114n includes all possible diagnostic/treatment regimes warranted by the values for disease variables 112a–112n, together with a corresponding priority assigned to the regime within that protocol grouping. Every protocol grouping 114a through 114n need not necessarily contain all possible diagnostic and treatment regimes, since governing medical standards will, in certain circumstances, rule out particular treatment regimes as entirely inappropriate given the measured test results in disease variables 112a–112n. However, protocol groupings 114a–114n are not intended to limit the health care provider's choice of treatment regimes. Therefore, even low percentage treatments (those which produce favorable outcomes in only a small fraction—say, 5% or less—of cases) for a given set of values in disease variables 112*a*–112*n* are included in the appropriate protocol grouping. The priorities assigned to the diagnostic and treatment regimes within a specific protocol grouping reflect the statistical probabilities of success determined through outcomes research.

The health care provider then chooses a diagnostic and treatment protocol from the protocol grouping selected based on the disease variable values. A code for the protocol choice selected and the associated priority for that protocol within the relevant protocol grouping may optionally be stored in protocol choice field (not shown). The health care provider is also prompted to enter a justification code 106, which reflects the rationale of the health care provider in selecting the chosen protocol. Justification code 106 is selected from a predefined set designated by the appropriate professional society, and uniquely identifies the protocol selected as well as the particular rationale for selecting the chosen protocol. Justification code 108 may include, for example, a code for a rationale such as "highest priority" to reflect that the selected protocol rates the highest priority in the relevant protocol grouping, "symptoms" to indicate that the health care provide believes the treatment is warranted by the symptoms, or "upper range(s)" to reflect that one or more disease variables is close to the next highest range employed to select protocol groupings.

Once the diagnostic or treatment regime (protocol) has been selected, the health care provider next selects particular diagnostic and/or treatment procedures from the selected protocol, together with a justification code from predefined sets 118*a*–118*n* for each procedure within the selected protocol. As with protocol justification codes, a particular procedure justification code uniquely identifies both the procedure selected and the rationale of the health care provider for selecting a procedure. The justification code entered by the health care provider for each diagnostic or treatment procedure selected is stored in procedure(s) justification field 108. Thus, procedure(s) justification field 108 may contain one or more codes, each for a different diagnostic or treatment procedure.

Finally, a CPT or DRG variable code 110 is included in data structure 102. CPT variable code 110 is a billing code identifying the procedures performed. Again, the appropriate professional society may develop the variants of the CPT codes which are employed. CPT code inaccuracy and abuse detection is enabled since the availability in the present invention of disease and protocol variables for cross-matching with CPT code variables permits significant analysis and filtering of CPT codes.

Figure 2A:
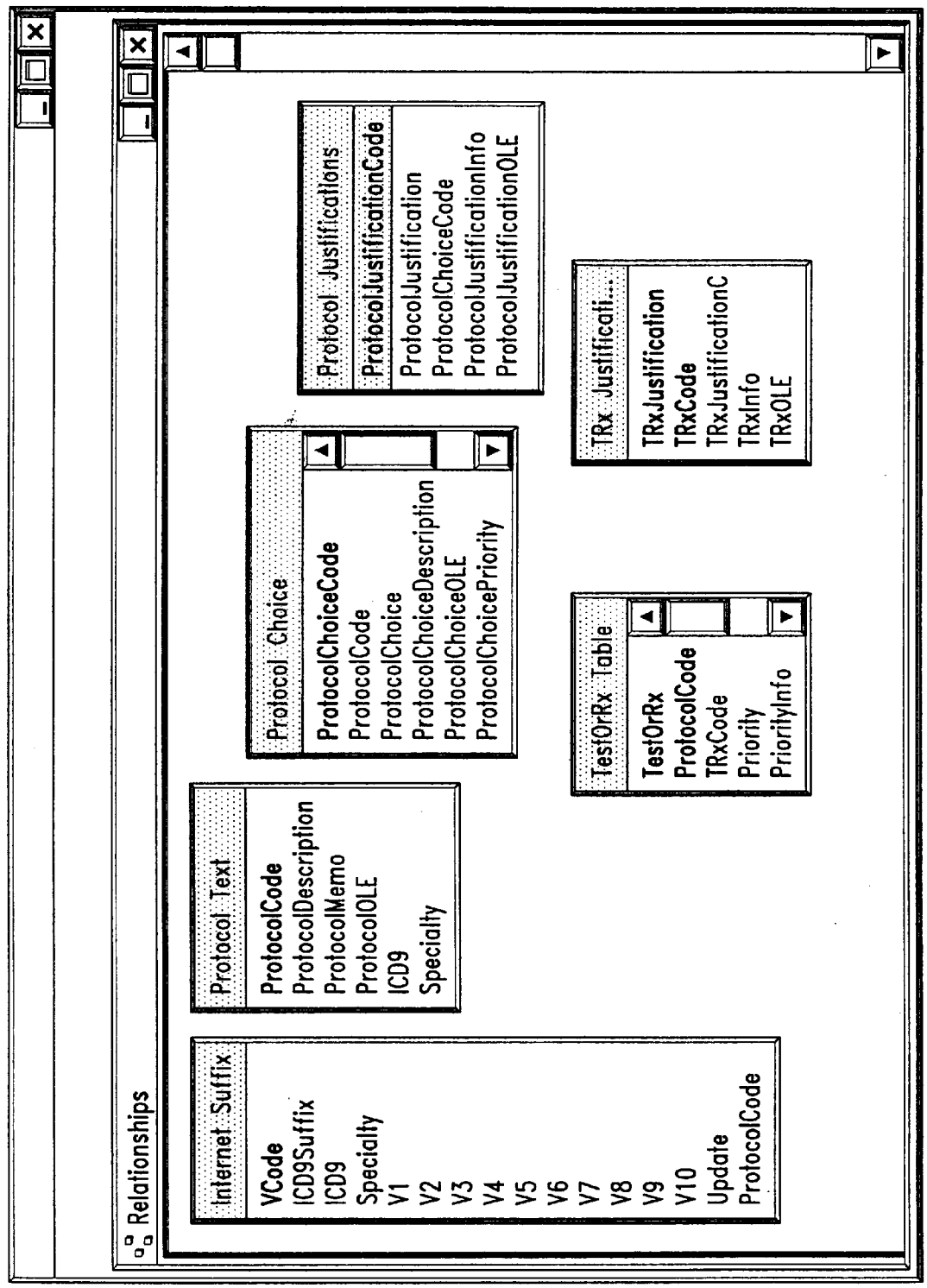
FIG. 2A is an entity relationship diagram for a relational database employed in formulating a diagnostic and treatment information data structure in accordance with a preferred embodiment of the present invention.

Referring to FIG. 2A, an entity relationship diagram for a relational database employed in formulating a diagnostic and treatment information data structure in accordance with a preferred embodiment of the present invention are illustrated. Data structure 102 encapsulating the diagnostic-treatment information is preferably formed through a structured data entry process in which a consistent vocabulary is employed. A relational database is preferably employed to guide the data entry process.

FIG. 2A depicts an entity relationship diagram for a exemplary relational database utilized to guide the health care provider in entering a protocol choice and justification into the appropriate fields of the diagnostic and treatment information data structure. The "Protocol Text" table is the parent table from which the protocol groupings are obtained for a particular specialty, and includes the fields listed below in Table I:

TABLE I

Protocol Text: Table

| Field Name | Data Type | Description |
|---|---|---|
| ProtocolCode | Text | Unique code for protocol |
| ProtocolDescription | Text | Protocol Grouping description |
| ProtocolMemo | Memo | Expanded information on grouping |
| ProtocolOLE | OLE Object | |
| ICD9 | Text | |
| Specialty | Text | |

The "ProtocolMemo" field provides additional information which may be selectively viewed by the health care provider, such as a description of the factors which influenced the decisions regarding priority assignments within the respective protocol group.

The disease variables V1 through V10 are input into a child table "Internet Suffix", which includes the fields listed below in Table II:

TABLE II

Internet Suffix: Table

| Field Name | Data Type | Description |
|---|---|---|
| VCode | Text | Shortened code of suffix |
| ICD9Suffix | Text | Defined suffix |
| ICD9 | Text | ICD9 Code |
| Specialty | Text | Medical specialty |
| V1 | Text | Variable #1 |
| V2 | Text | Variable #2 |
| V3 | Text | Variable #3 |
| V4 | Text | Variable #4 |
| V5 | Text | Variable #5 |
| V6 | Text | Variable #6 |
| V7 | Text | Variable #7 |
| V8 | Text | Variable #8 |
| V9 | Text | Variable #9 |
| V10 | Text | Variable #10 |
| Update | Date/Time | Date updated field |
| ProtocolCode | Text | |

The "Internet Suffix" table determines the "VCode" for the disease variable combinations, and also determines the appropriate ICD9 code. The appropriate protocol grouping may then be displayed for the user to make a protocol choice.

The "Protocol Choice" child table generates codes for the user-selected protocol choice to be entered into the protocol choice code field of the diagnostic and treatment information data structure with the fields listed in Table III:

TABLE III

Protocol Choice: Table

| Field Name | Data Type | Description |
|---|---|---|
| ProtocolChoiceCode | Text | Unique code of protocol |
| ProtocolCode | Text | |
| ProtocolChoice | Text | Label of choice |
| ProtocolChoiceDescription | Text | |
| ProtocolChoiceOLE | OLE Object | |
| ProtocolChoicePriority | Text | Priority score from medical society |
| ProtocolCodeHyperlink | Hyperlink | |

A justification for the selected protocol choice is obtained from a "Protocol Justifications" child table including the fields listed in Table IV:

TABLE IV

Protocol Justification: Table

| Field Name | Data Type | Description |
| --- | --- | --- |
| ProtocolJustificationCode | Text | Unique code |
| ProtocolJustification | Text | |
| ProtocolChoiceCode | Text | |
| ProtocolChoiceDescription | Text | |
| ProtocolJustificationInfo | Memo | |
| ProtocolJustificationOLE | OLE Object | |

As part of the selection of a protocol, the health care provider may specify particular treatments or diagnostic tests within the protocol grouping selected. The specific diagnostic test(s) and/or treatment(s) specified, together with a justification code for those diagnostic test(s) and/or treatment(s), are input into the "Protocol Text" "TRx Justification Table" child table, which include the fields listed in Tables V and VI, respectively:

TABLE V

TestOrRx Table: Table

| Field Name | Data Type | Description |
| --- | --- | --- |
| TestOrRx | Text | |
| ProtocolCode | Text | |
| TRxCode | Text | |
| Priority | Text | |
| PriorityInfo | Memo | |
| Grouping | Text | |
| Category | Text | |
| TestOrRxHyperlink | Hyperlink | |

TABLE VI

TRx Justification Table: Table

| Field Name | Data Type | Description |
| --- | --- | --- |
| TRxJustification | Text | |
| TRxCode | Text | |
| TRxJustificationCode | Text | |
| TRxInfo | Text | |
| TRxOLE | OLE Object | |

The individual diagnostic and treatment regimes within the protocol grouping which are selected by the health care provider are justified and encoded into the protocol choice and justification fields of the diagnostic and treatment information data structure.

Finally, a "CPTVariableCode" table with the fields listed in Table VII below provides the CPT variable code. These codes described the specific variables utilized in deriving the correct billing charge (CPT code).

TABLE VII

CPTVariableCode: Table

| Field Name | Data Type | Description |
| --- | --- | --- |
| VCPTCode | Text | |
| CPT | Text | |
| Specialty | Text | |
| TechOrProf | Text | |
| Category | Text | |
| vCPT1 | Text | |
| vCPT2 | Text | |

TABLE VII-continued

CPTVariableCode: Table

| Field Name | Data Type | Description |
| --- | --- | --- |
| vCPT3 | Text | |
| vCPT4 | Text | |
| vCPT5 | Text | |
| vCPT6 | Text | |

Figure 2B:
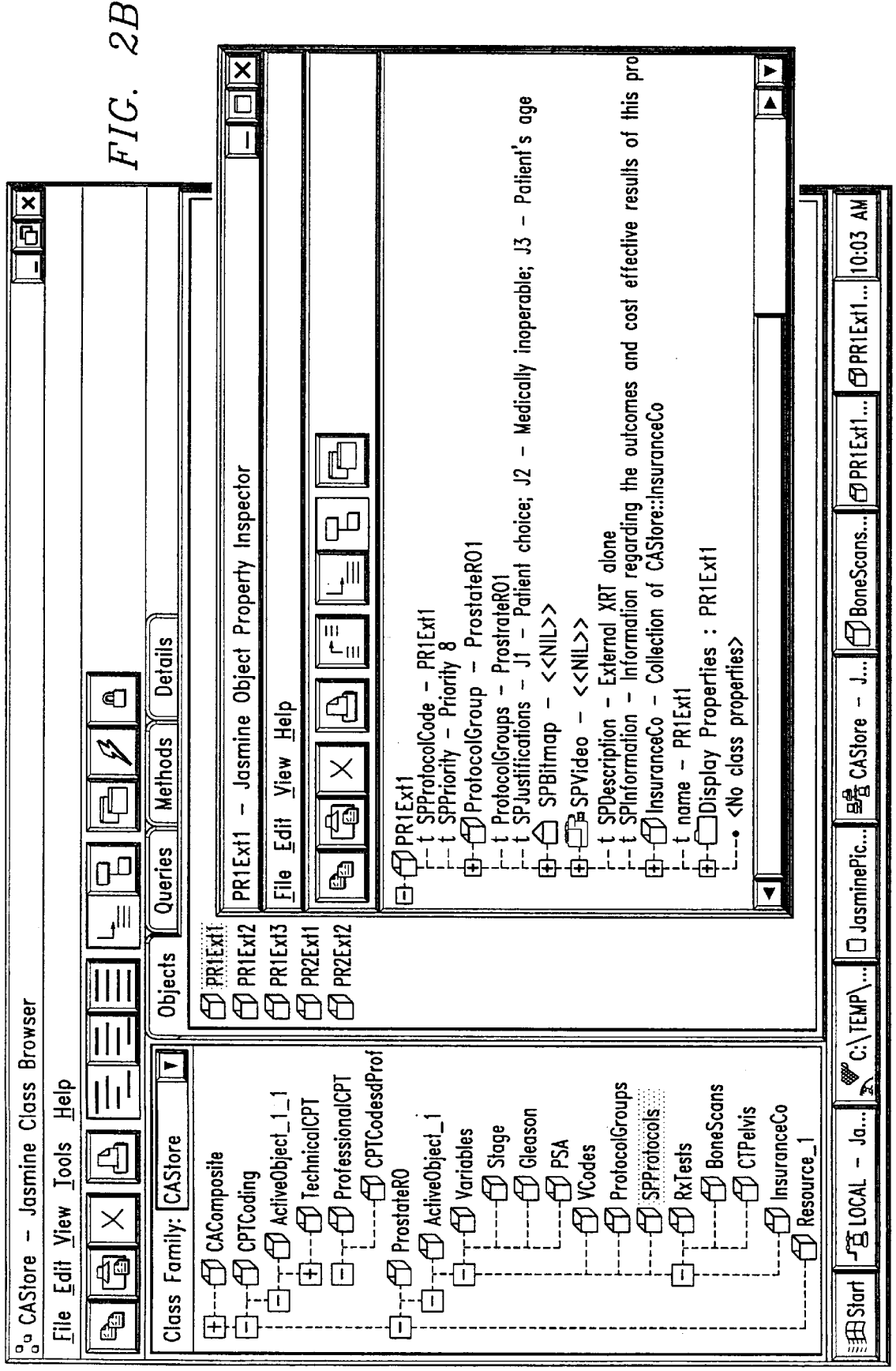
FIG. 2B is an Object Oriented Database Management System Model diagram employed in formulating a diagnostic and treatment information data structure in accordance with a preferred embodiment of the present invention.

The relational database described above provides the analysis tool and may also be employed for the data entry user interface. The various code definitions employed may be modelled as an object oriented database for Internet presentation Referring to FIG. 2B, an Object Oriented Database Management System Model diagram employed in formulating a diagnostic and treatment information data structure in accordance with a preferred embodiment of the present invention is illustrated. The user interface screen capture shown in FIG. 2B illustrates the hierarchical arrangement of database fields for protocols. The background screen capture illustrates a hierarchy for prostate cancer ("ProstateRO"), under which are the disease variables ("Variables", including "Stage", "Gleason" and "PSA"), the Vcodes ("VCodes"), the protocol definitions ("SPProtocols"), and the treatment and testing regimes ("RxTests", including "BoneScans" and "CTPelvis"). The protocol groupings ("SPProtocols") on the left maps to a number of protocol definitions ("PR1xt1", "PR1xt2", "PR1xt3", "PR2Ext1", "PR2Ext2", etc.) on the right. Additionally, the hierarchy may include insurance company billing and authorization information ("InsuranceCo").

The screen capture in the foreground of FIG. 2B illustrates the information forming a protocol definition (specifically "PR1xt1"). This includes the protocol code ("SPProtocolCode"), priority ("SPPriority"), and description ("SPDescription"), the defined justification codes ("SPJustifications"), information regarding outcomes study results and cost effectiveness ("SPInformation"), and insurance information ("InsuranceCo").

With reference now to FIG. 3, a high level flowchart for a process of formulating a diagnostic and treatment information data structure in accordance with a preferred embodiment of the present invention is depicted. The process begins at step 302, which depicts data entry into a diagnostic and treatment information data structure being initiated. The process then passes to step 304, which illustrates retrieving test result values of the relevant disease variables for the specialty under which the data entry is being performed and determining the appropriate protocol grouping. The set of disease variables is defined for each specialty and the test values may be extracted, for example, from an electronic patient record. The test values are compared to defined ranges as described above to determine which protocol grouping is appropriate. Each disease variable code uniquely identifies a single protocol grouping to which the disease variable ranges map. The protocol grouping, listing diagnostic and treatment protocols in order of priority, may then be displayed to the user.

The process next passes to step 306, which depicts prompting the user for the protocol choice justification. The protocol choice is not automatic, but must be selected by the health care provider. The justification selected uniquely identifies both the protocol selected by the health care provider and the rationale for making such selection. The protocol choice justification need only be selected once for a particular disease process.

The process passes next to step 308, which illustrates a determination of whether the user has selected a protocol choice justification. If not, the process returns to step 308 to continue awaiting user selection of a protocol choice justification. If so, however, the process proceeds instead to step 310, which depicts prompting the user for diagnostic or treatment procedure(s) justification(s) for the diagnostic and treatment procedures selected by the health care provider. The different diagnostic and treatment procedure(s) justification(s) may be entered over a period of time, recorded as each diagnosis and/or therapy is undertaken.

The process next passes to step 312, which illustrates a determination of whether the user has completed selection of procedure(s) justification(s) for the specific diagnostic test and treatments selected within a protocol choice. If not, the process returns to step 312 to continue awaiting user entry of additional justifications. If so, however, the process proceeds instead to step 314, which depicts determining the correct CPT variable code. The CPT variable code may be a composite of multiple CPT codes, each for a different diagnostic or treatment procedure.

The process then passes to step 316, which illustrates combining codes for: (1) the disease variable value ranges; (2) the protocol choice justification selected by the user; (3) the specific diagnostic testing and treatment procedures justifications selected by the user; and (4) the CPT variant determined by the CPT codes for the diagnostic and treatment procedures performed. These code may be combined as discrete objects within a container object or as either a delimited character string or a single character string code having defined field sizes. The character strings representing the combined codes may be electronic, printed, or both. A code identifying the medical service provider and specialty may be appended. The process finally proceeds to step 318, which depicts the process becoming idle until data entry is again initiated for a diagnostic and treatment information data structure in accordance with the present invention.

The process depicted in FIG. 3 is merely exemplary for the purposes of explaining the present invention, and those skilled in the art will recognize that numerous variants are possible. Procedures depicted as combined in a single step in the example of FIG. 3 may be performed separately, and procedures depicted as separate steps may be combined. The order in which procedures are performed is not critical, except where a particular portion of the process is dependent on a prior portion. No limitations are intended to be implied by the example shown.

Figure 4A:
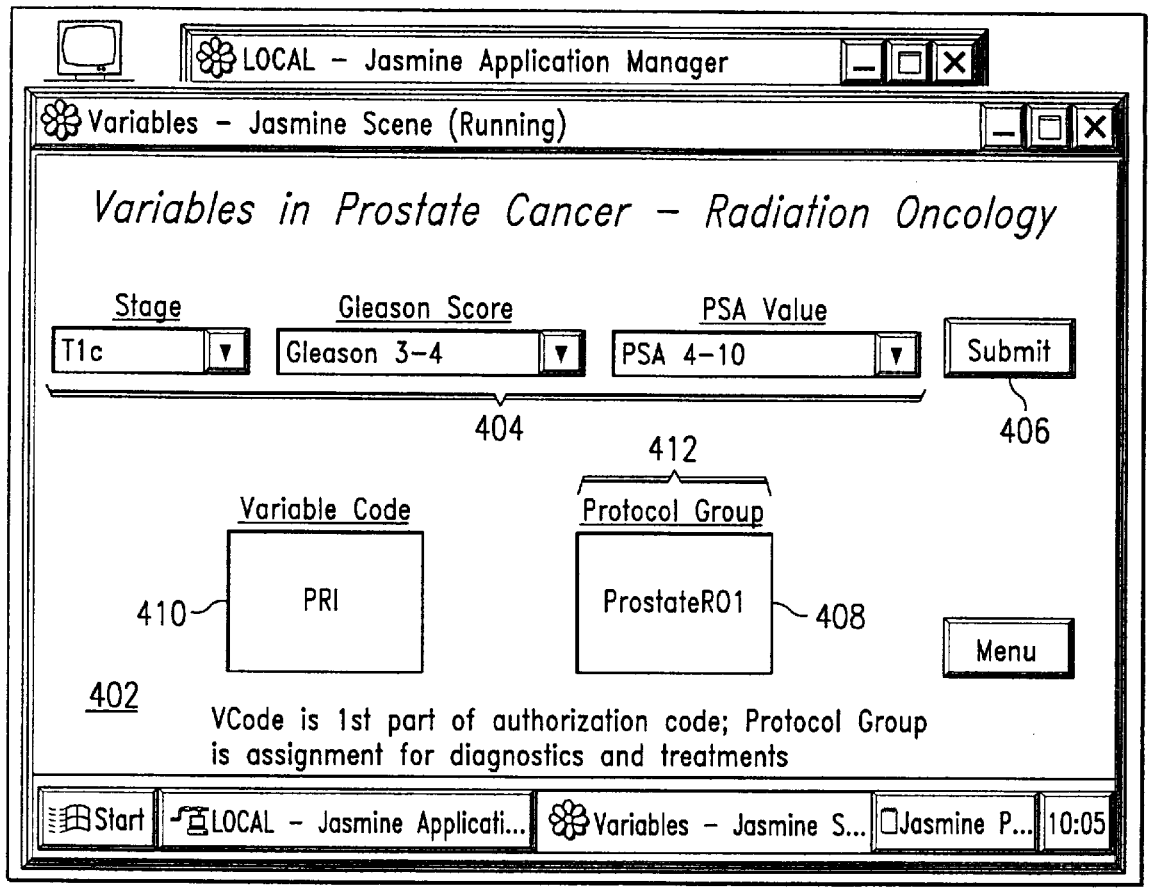
FIGS. 4A 4B and 4C are user interface diagrams for a software application for formulating a diagnostic and treatment information data structure in accordance with a preferred embodiment of the present invention.
Figure 4B:
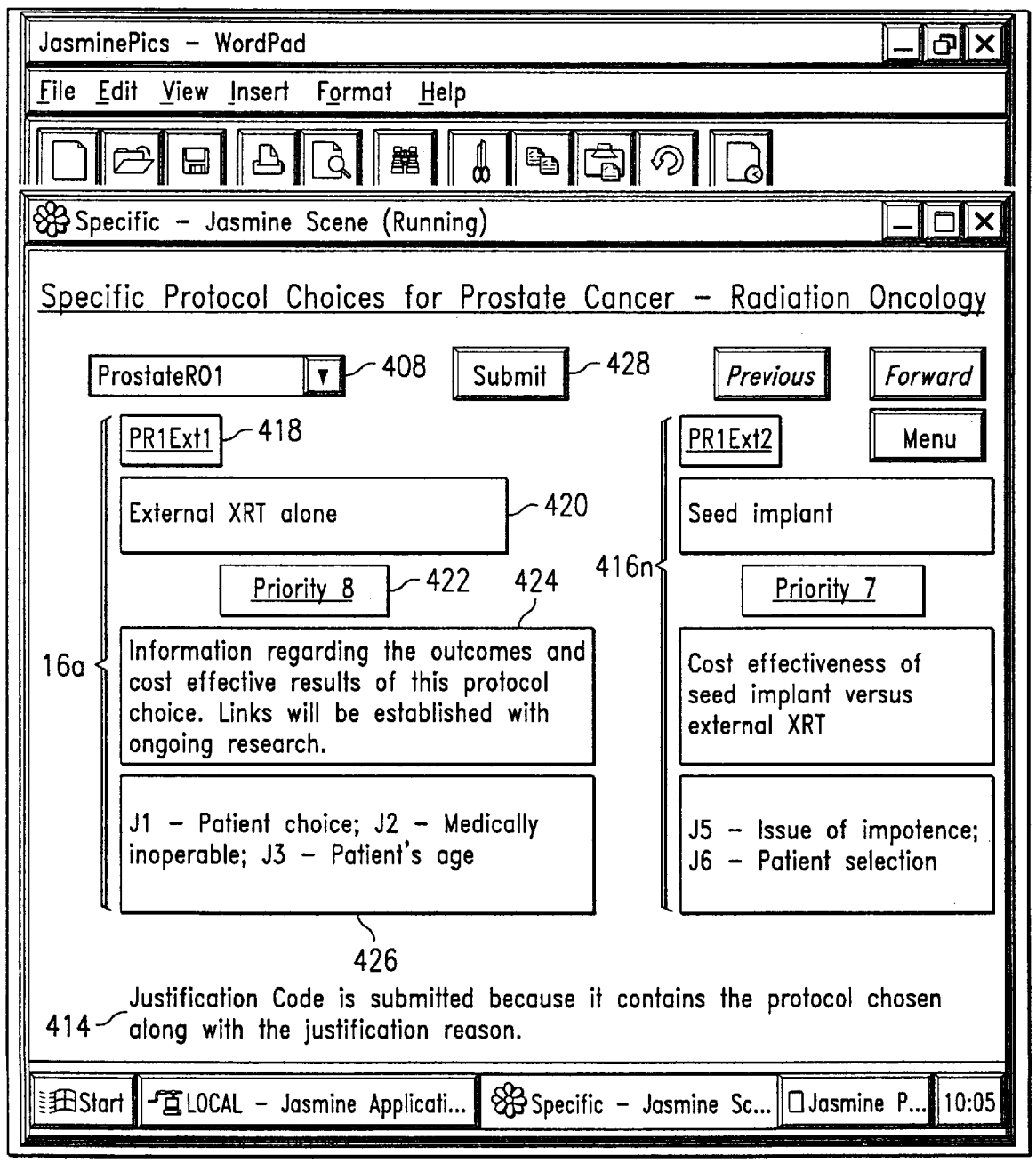
Figure 4C:
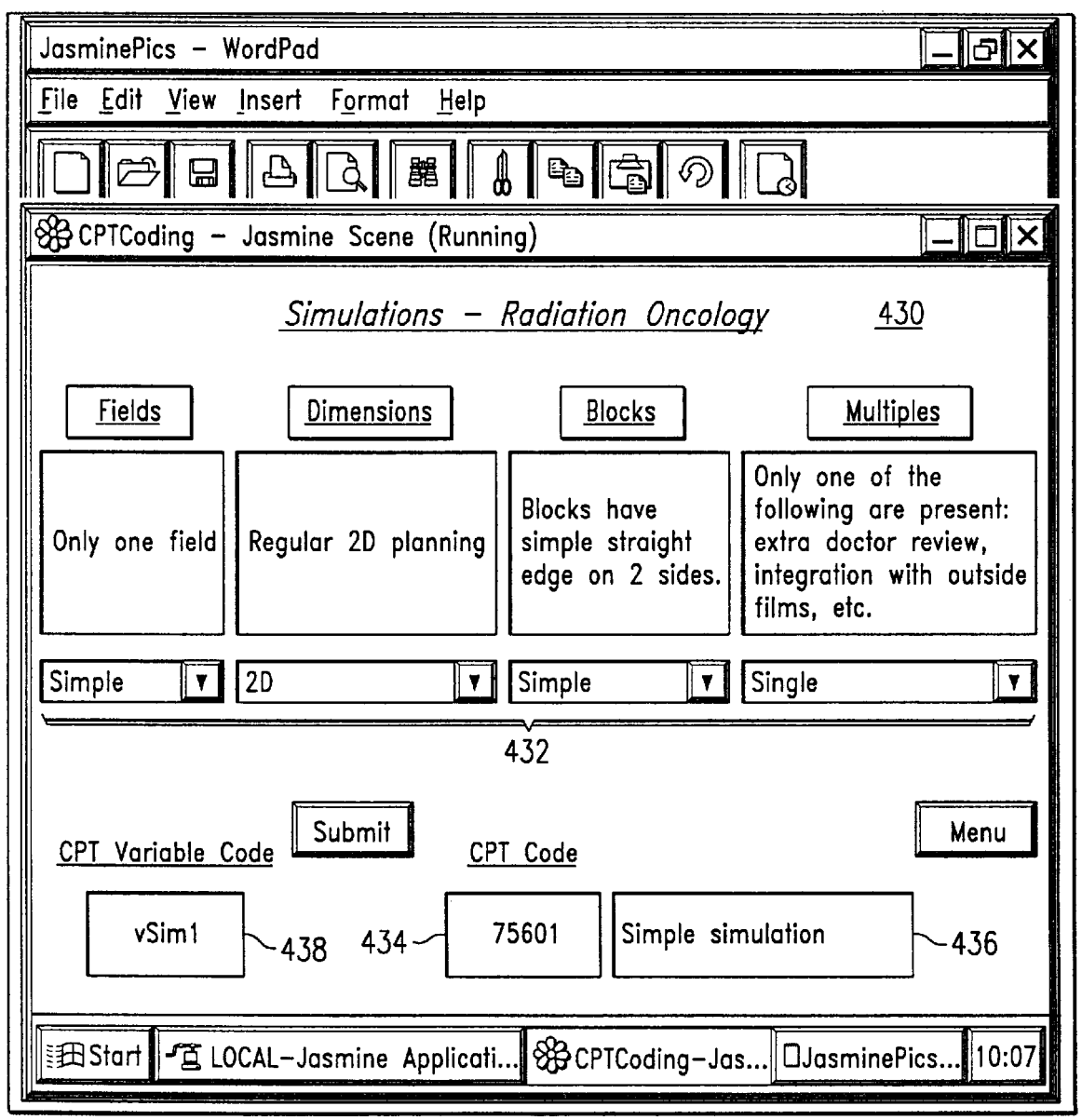

Referring to FIGS. 4A–4C, user interface diagrams for a software application for formulating a diagnostic and treatment information data structure in accordance with a preferred embodiment of the present invention are illustrated. The user interface diagrams shown are for a software application employing an object-oriented database of the type described above in connection with FIG. 2 and Tables I–VII and performing a process substantially similar to that shown in FIG. 3.

A first user interface display 402 contains a plurality of disease variable data entry fields 404 defined for the relevant specialty, in which the test values for the disease variables V1, V1, V3, etc. through V10, if necessary, may be entered. A user control 406, which is a button in the depicted example, causes the software to operate on the entered variable values to determine the corresponding protocol grouping, which may be displayed as ProtocolCode 408 and VCode 410. A second user control 412, a hyperlink in the depicted example, allows the user to view a display containing the protocol choices, priorities, and justifications for the identified protocol grouping.

Actuation of user control 412 causes the software to display a second user interface display 414 containing protocol choice information groupings 416a–416n. Each protocol choice information grouping 416a–416n includes, for the protocol grouping identified by ProtocolCode 408, a ProtocolChoiceCode field 418 displaying the protocol choice code for the corresponding protocol choice, a Protocolfield 420 displaying a brief description of the corresponding protocol choice, a ProtocolChoicePriority field 422 displaying the priority of the corresponding protocol choice within the identified protocol grouping, a display 424 of information regarding the corresponding protocol choice and/or comparative information with respect to other protocol choices within the identified protocol grouping, and a display 426 of defined justifications for the corresponding protocol choice.

The user may select a protocol choice and justification within those displayed for the identified protocol grouping by actuating a pointing device while a cursor (not shown) is displayed within an area of the user interface display 412 occupied by the protocol choice information grouping 416a–416n associated with the desired protocol choice. A visual cue as to the user'sprotocol choice selection may be provided by highlighting the ProtocolChoiceCode field 418 of the selected protocol choice. A user control 428 is provided for the user to submit the selected protocol choice. The user will then be prompted to select a justification code from those listed in display 426.

Actuation of user control 428 causes the software to display a third user interface display 430 containing specific diagnostic or treatment regime information 432 for the selected protocol choice. This will include, for instance, justifications for selecting particular diagnostic or treatment procedures. If appropriate, user interface display 430 may also display the CPT code 434 and description 436 for the selected protocol choice and diagnostic and treatment regime, as well as the CPT variable code 438.

The software application employing the user interfaces described above and depicted in FIGS. 4A–4C guides the health care provider through data entry for a diagnostic and treatment information data structure in accordance with the present invention. It also provides an opportunity to guide the health care providers decision by identifying medically-accepted priorities for particular protocol choices given disease variable values and supplying direct and/or comparative information for each protocol choice which is dependent on the disease variable values. This information may includes outcomes study results, cost effectiveness information, or other suitable information.

Figure 5:
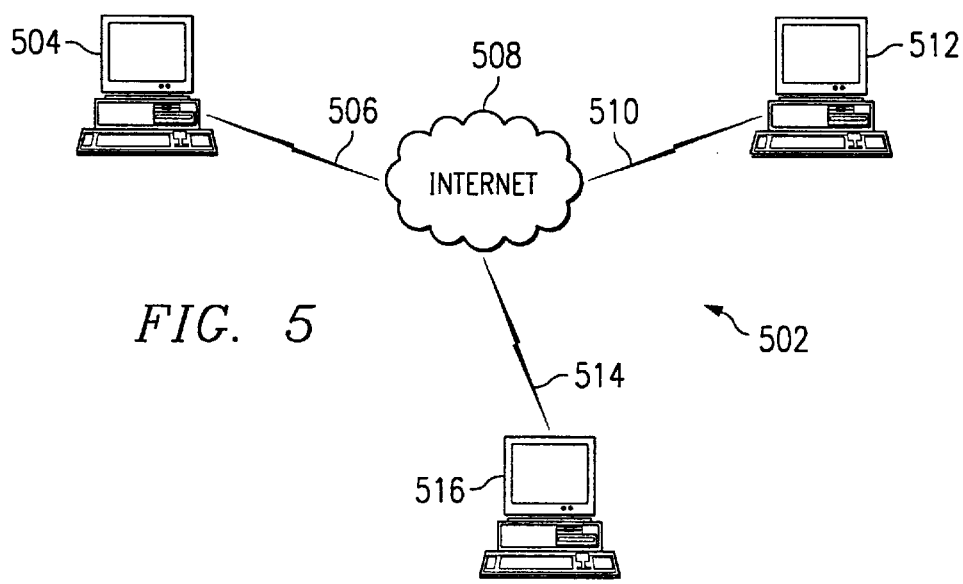
FIG. 5 is a diagram of a data processing system network in which the diagnostic and treatment information data structure in accordance with a preferred embodiment of the present invention may be employed.

With reference now to FIG. 5, a diagram of a data processing system network in which the diagnostic and treatment information data structure in accordance with a preferred embodiment of the present invention may be employed is depicted. Data processing system network 502 includes a health care provider data processing system 504 in which the diagnostic and treatment information data structure of the present invention is formulated for a particular diagnosis-treatment cycle. Data processing system 504 is coupled by communications link 506 to the Internet 508, which is coupled in turn to medical society data processing system 512 by communications link 510 and to insurance company data processing system 516 by communications link 514. Data processing systems 504, 512, and 516 and communications links 506, 510 and 514 may be any suitable data processing system or communications link known in the art.

With data processing system network 502, the diagnosis and treatment information data structure for a particular diagnosis treatment cycle may be shared by the health care provider with the relevant medical society or societies and the insurance company or companies. No patient-identifying information is contained within the diagnosis and treatment information data structure of the present invention, thus protecting the patient'sconfidentiality. The diagnosis and treatment information data structures for various diagnosis-treatment cycles may be collected and combined in a database for analysis. Since the underlying disease variable information, the rationale of the health care provider, and the outcomes measurements for a specific diagnosis-treatment cycle are all available within each diagnosis and treatment information data structure, the information may be effectively analyzed utilizing known statistical methods to determine effectiveness, outcomes probabilities, and absolute or relative cost effectiveness.

Medical societies for specialties treating particular diseases, such as breast cancer, prostate cancer, lung cancer, colon/rectum cancer, the lymphomas, diabetes, congestive heart failure, asthma, and the like may each maintain databases of diagnosis and treatment information data structures submitted by members or insurance companies. These databases may be employed to define or refine protocol groupings and the protocol choice priorities within each protocol groupings. Periodic review may be performed to generate updates provided to members and to attempt to identify previously undiscovered trends.

Insurance companies may employ the collected data to perform cost analyses and to assist in negotiating capitated contracts. Compensation schemes for particular protocol choices and justifications may be established, such as requiring patient payment for treatments which have low probabilities of success but which are chosen by the patient over other treatments having higher probabilities of success. Importantly, the CPT variable code may be cross-correlated and checked against the protocol choice and selected diagnosis and treatment procedures for inaccuracy or appropriateness.

Health care providers may be provided within information from medical societies or insurance companies within the user interface of applications formulating the diagnosis and treatment information data structure for a particular patient. This information may thus be brought to influence the health care provider at the point of decision. Regional and national outcomes information, as well as treatment variant success rates, may also be accessed by the health care provider in selecting a protocol choice.

It is important to note that while the present invention has been described in the context of a fully functional data processing system, network, and/or system of networks including internets, intranets, extranets, etc., those skilled in the art will appreciate that the mechanism of the present invention is capable of being distributed in the form of a computer usable medium of instructions in a variety of forms, and that the present invention applies equally regardless of the particular type of signal bearing media used to actually carry out the distribution. Examples of computer usable media include: nonvolatile, hard-coded type mediums such as read only memories (ROMs) or erasable, electrically programmable read only memories (EEPROMs), recordable type mediums such as floppy disks, hard disk drives and CD-ROMs, and transmission type media such as digital and analog communication links.

The description of the preferred embodiment of the present invention has been presented for purposes of illustration and description, but is not intended to be exhaustive or limit the invention in the form disclosed. Many modifications and variations will be apparent to those of ordinary skill in the art. The embodiment was chosen and described in order to best explain the principles of the invention and the practical application to enable others of ordinary skill in the art to understand the invention for various embodiments with various modifications as are suited to the particular use contemplated.

What is claimed is:

1. A data structure stored in a computer-readable medium, to be read by a microprocessor comprising:
    a first code uniquely identifying a protocol grouping assigning priorities to one or more protocol choices based on a range of one or more disease variable values;
    a second code identifying a protocol choice selected from the protocol grouping and a justification for selecting the protocol choice;
    a third code identifying each procedure, diagnostic test, or treatment performed pursuant to the protocol choice and a justification for selecting each respective procedure, diagnostic test, or treatment; and
    a fourth code defining a charge code for all procedures, diagnostic tests, and treatments performed.

2. The data structure stored in a computer-readable medium of claim 1, further comprising:
    a fifth code identifying a medical provider and specialty.

3. The data structure stored in a computer-readable medium of claim 1, wherein the third code further comprises:
    an outcome code for results of the procedure, diagnostic test or treatment performed.

4. The data structure stored in a computer-readable medium of claim 1, further comprising:
    at least one disease variable value for a testing result, wherein a range within which the disease variable value falls is employed to select the first code.

5. The data structure stored in a computer-readable medium of claim 1, wherein the protocol grouping identified by the first code includes a plurality of protocol choices, each protocol choice assigned a priority which is unique within the protocol grouping by a medical oversight organization.

6. The data structure stored in a computer-readable medium of claim 1, wherein comparison of the third and fourth codes identifies discrepancies in treatment and billing information.

7. A method of processing medical treatment information, to be read by a microprocessor comprising:
    comparing test result values to ranges defined for mapping the test results to a protocol grouping assigning priorities to one or more protocol choices within the protocol grouping;
    storing a first code in a data structure which identifies a protocol grouping identified by comparing the test results to the defined ranges;
    storing a second code in the data structure uniquely identifying a selected protocol choice within the identified protocol grouping and a justification for the protocol choice selection;
    storing a third code in the data structure identifying each procedure, diagnostic test, or treatment performed pursuant to the selected protocol choice and a justification for selecting each respective procedure, diagnostic test, or treatment; and
    storing a fourth code in the data structure identifying charges for all procedures, diagnostic tests, and treatments performed.

8. The method of claim 7, further comprising:

responsive to identifying a protocol grouping by comparing the test results to the defined ranges, displaying each protocol choice within the identified protocol grouping together with an associated priority assigned to each respective protocol choice.

9. The method of claim 8, further comprising:

for each protocol choice within the identified protocol grouping, displaying a set of defined justifications for selecting that protocol choice.

10. The method of claim 7, further comprising:

responsive to selection of a protocol choice within the identified protocol grouping, displaying all procedures, diagnostic tests, and treatments for the selected protocol choice together with associated justifications for each procedure, diagnostic test, and treatment.

11. The method of claim 10, further comprising:

selectively displaying information regarding outcomes or cost effectiveness for a procedure, diagnostic test, treatment within the selected protocol choice.

12. The method of claim 10, further comprising:

selectively displaying insurance payment information for a procedure, diagnostic test, treatment within the selected protocol choice.

13. The method of claim 7, further comprising:

appending a fifth code identifying a medical provider and specialty to the data structure.

14. The method of claim 7, further comprising:

transmitting the data structure to a medical organization data collection server.

15. The method of claim 7, further comprising:

transmitting the data structure to an insurance company billing server.

16. A system for processing medical treatment information, to be read by a microprocessor comprising:

a data processing system;

a database within the data processing system containing a plurality of protocol groupings each assigning priorities to one or more protocol choices within the protocol groupings and ranges defined for mapping the test result values to a protocol grouping within the plurality of protocol groupings; and a data structure within the data processing system, the data structure including:

a first code specifying a protocol grouping identified by comparing measured test result values to the defined ranges;

a second code uniquely identifying a selected protocol choice within the identified protocol grouping and a justification for the protocol choice selection;

a third code identifying each procedure, diagnostic test, or treatment performed pursuant to the selected protocol choice and a justification for selecting each respective procedure, diagnostic test, or treatment; and a fourth code identifying charges for all procedures, diagnostic tests, and treatments performed.

17. The system of claim 16, further comprising:

an application executing within the data processing system for creating the data structure, the application:

displaying each protocol choice within an identified protocol grouping together with an associated priority in response to identifying the protocol grouping by comparing the test results to the defined ranges;

displaying, for each protocol choice within the identified protocol grouping, a set of defined justifications for selecting a respective protocol choice;

displaying, in response to selection of a protocol choice within the identified protocol grouping, all procedures, diagnostic tests, and treatments for the selected protocol choice together with associated justifications for each procedure, diagnostic test, and treatment;

selectively displaying information regarding outcomes or cost effectiveness for a procedure, diagnostic test, treatment within the selected protocol choice; and selectively displaying insurance payment information for a procedure, diagnostic test, treatment within the selected protocol choice.

18. The system of claim 16, further comprising:

a medical organization server coupled to the data processing system and serving requests from the data processing system for information regarding outcomes or cost effectiveness for a procedure, diagnostic test, treatment within the selected protocol choice.

19. The system of claim 16, further comprising:

an insurance company server coupled to the data processing system and serving requests from the data processing system for insurance payment information for a procedure, diagnostic test, treatment within the selected protocol choice.

20. The system of claim 16, further comprising:

a communications facility within the data processing system, the communications facility:

appending a fifth code identifying a medical service provider and specialty to the data structure; and transmitting the data structure to an insurance company billing server.

* * * * *